(12) United States Patent
Ewert et al.

(10) Patent No.: US 7,157,612 B2
(45) Date of Patent: Jan. 2, 2007

(54) OLEFIN PRODUCTION PROCESS

(75) Inventors: Warren M. Ewert, Bartlesville, OK (US); William M. Woodard, Bartlesville, OK (US); Harvey D. Hensley, Bartlesville, OK (US); Mark E. Lashier, Bartlesville, OK (US); Glyndal D. Cowan, Bartlesville, OK (US); Jeffrey W. Freeman, Bartlesville, OK (US); Ralph V. Franklin, Nowata, OK (US); Ronald D. Knudsen, Bartlesville, OK (US); Richard L. Anderson, Bartlesville, OK (US); Lyle R. Kallenbach, Bartlesville, OK (US); Bruce E. Kreischer, Bartlesville, OK (US)

(73) Assignee: Phillips Petroleum Company, Bartlesville, OK (US)

( * ) Notice: Subject to any disclaimer, the term of this patent is extended or adjusted under 35 U.S.C. 154(b) by 0 days.

(21) Appl. No.: 10/872,250

(22) Filed: Jun. 18, 2004

(65) Prior Publication Data

US 2004/0228775 A1 Nov. 18, 2004

Related U.S. Application Data

(62) Division of application No. 08/951,201, filed on Oct. 14, 1997.

(51) Int. Cl.
C07C 2/26 (2006.01)
C07C 2/30 (2006.01)

(52) U.S. Cl. ............... 585/511; 585/510; 585/512; 585/513; 585/522; 585/523; 585/527

(58) Field of Classification Search ............ 585/510, 585/511, 512, 513, 522, 523, 527
See application file for complete search history.

(56) References Cited

U.S. PATENT DOCUMENTS

| | | | |
|---|---|---|---|
| 5,288,823 A | 2/1994 | Reagan et al. | |
| 5,331,104 A | 7/1994 | Reagen et al. | |
| 5,376,612 A | 12/1994 | Reagen et al. | |
| 5,470,926 A | 11/1995 | Reagen et al. | |
| 5,523,507 A | 6/1996 | Reagen et al. | |
| 5,563,312 A * | 10/1996 | Knudsen et al. | 585/513 |
| 5,750,816 A * | 5/1998 | Araki et al. | 585/512 |
| 5,856,612 A * | 1/1999 | Araki et al. | 585/522 |
| 5,910,619 A * | 6/1999 | Urata et al. | 585/513 |
| 6,133,495 A | 10/2000 | Urata et al. | |
| 6,455,648 B1 | 9/2002 | Freeman et al. | |

FOREIGN PATENT DOCUMENTS

WO    WO 9733924 A1 *  9/1997

\* cited by examiner

*Primary Examiner*—Thuan D Dang
(74) *Attorney, Agent, or Firm*—Womble Carlyle Sandridge & Rice, PLLC

(57) ABSTRACT

A process is provided to stabilize and/or reactivate an olefin production catalyst system which comprises contacting an olefin production catalyst system, either before or after use, with an aromatic compound.

49 Claims, 6 Drawing Sheets

OLEFIN PRODUCTION PROCESS

CROSS-REFERENCE TO RELATED APPLICATION

This application is a divisional application of co-pending U.S. patent application Ser. No. 08/951,201 filed Oct. 14, 1997, which is incorporated herein in its entirety by reference.

BACKGROUND OF THE INVENTION

This invention relates to olefin production and olefin production process improvements.

Olefins, primarily alpha olefins, have many uses. In addition to uses as specific chemicals, alpha-olefins, especially mono-1-olefins, are used in polymerization processes either as monomers or comonomers to prepare polyolefins, or polymers. These alpha-olefins usually are used in a liquid or gas state. Unfortunately, very few efficient processes to selectively produce a specifically desired alpha-olefin are known.

SUMMARY OF THE INVENTION

Accordingly, it is an object of this invention to provide an improved olefin production process.

It is another object of this invention to provide an olefin production process which will provide high purity 1-hexene.

It is a further object of this invention to provide an olefin production process which can be used in conjunction with other processes that utilize trimerization reaction reactants and/or reaction products.

In accordance with this invention, a process is provided to trimerize olefins comprising, in combination a) a reactor, b) at least one inlet line into said reactor for olefin reactant and catalyst system, c) effluent lines from said reactor for trimerization reaction products, and d) at least one separator to separate desired trimerization reaction products; wherein said catalyst system comprises a chromium source, a pyrrole-containing compound and a metal alkyl.

In accordance with another embodiment of this invention, a process is provided to trimerize ethylene comprising, in combination a) a reactor, b) at least one inlet line into said reactor for ethylene reactant and catalyst system, c) effluent lines from said reactor for trimerization reaction products, and d) at least one separator to separate desired 1-hexene reaction product; wherein said catalyst system comprises a chromium source, a pyrrole-containing compound, a metal alkyl, and optionally a halide source.

In accordance with yet another embodiment of this invention, a process is provided to trimerize olefins consisting essentially of, in combination a) a reactor, b) at least one inlet line into said reactor for olefin reactant and catalyst system, c) effluent lines from said reactor for trimerization reaction products, and d) at least one separator to separate desired trimerization reaction products; wherein said catalyst system comprises a chromium source, a pyrrole-containing compound and a metal alkyl.

BRIEF DESCRIPTION OF THE DRAWINGS

In the drawings, forming a part hereof, wherein like reference characters denote like parts in the various figures.

DETAILED DESCRIPTION OF THE INVENTION

Catalyst Systems

Figure 1:
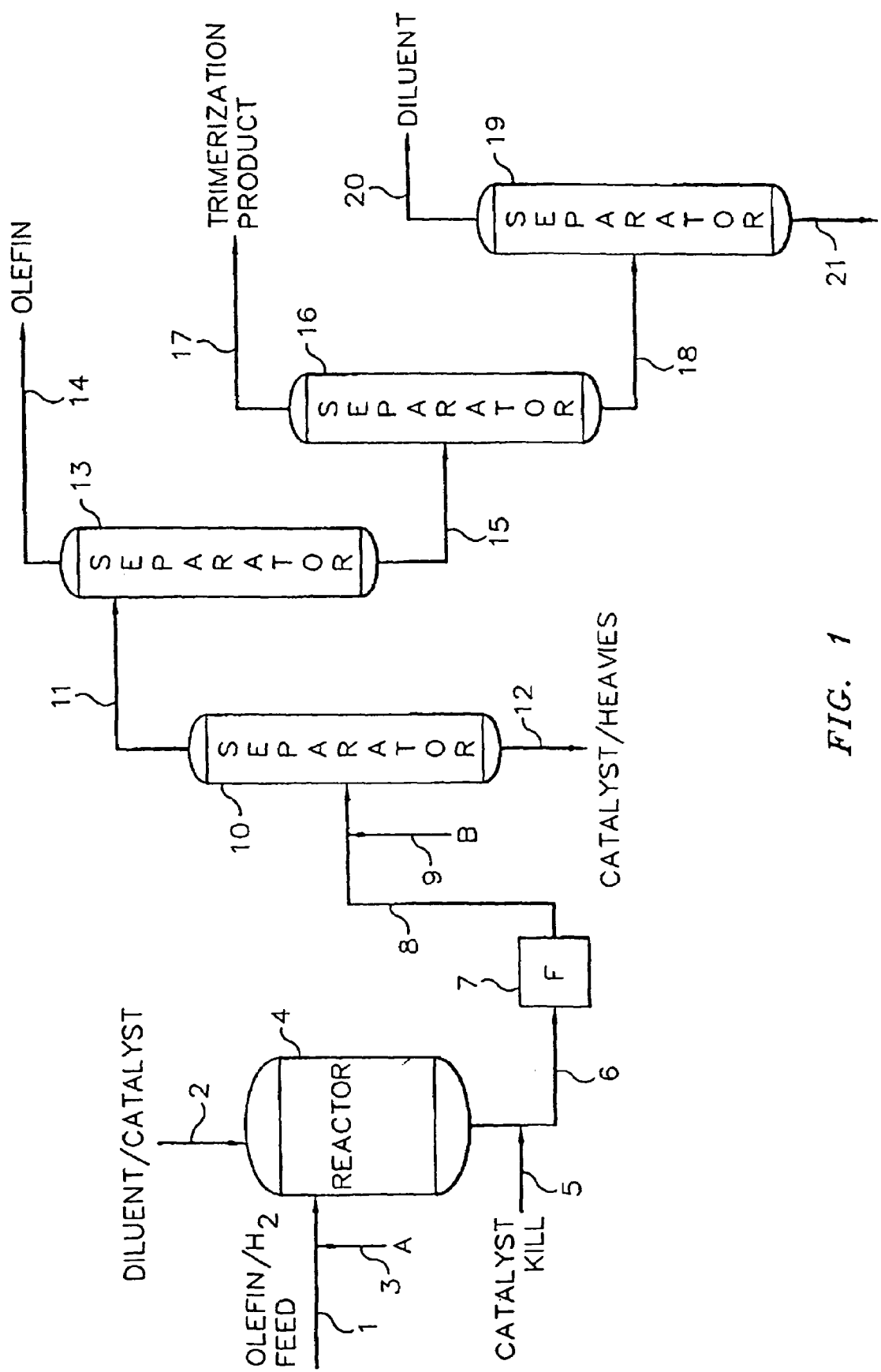
FIG. 1 is a schematic representation of one embodiment of an olein trimerization process using four separators, wherein two of said separators are used following olefin removal.

Catalyst systems useful in accordance with this invention comprise a chromium source, a pyrrole-containing compound and a metal alkyl, all of which have been contacted and/or reacted in the presence of an unsaturated hydrocarbon. Optionally, these catalyst systems can be supported on an inorganic oxide support. These catalyst systems are especially useful for the dimerization and trimerization of olefins, such as, for example, trimerization of ethylene to 1-hexene.

The chromium source can be one or more organic or inorganic compounds, wherein the chromium oxidation state is from 0 to 6. Generally, the chromium source will have a formula of $CrX_n$, wherein X can be the same or different and can be any organic or inorganic radical, and n is an integer from 1 to 6. Exemplary organic radicals can have from about 1 to about 20 carbon atoms per radical, and are selected from the group consisting of alkyl, alkoxy, ester, ketone, and/or amido radicals. The organic radicals can be straight-chained or branched, cyclic or acyclic, aromatic or aliphatic, can be made of mixed aliphatic, aromatic, and/or cycloaliphatic groups. Exemplary inorganic radicals include, but are not limited to halides, sulfates, and/or oxides.

Preferably, the chromium source is a chromium(II)-and/or chromium(III)-containing compound which can yield a catalyst system with improved trimerization activity. Most preferably, the chromium source is a chromium(III) compound because of ease of use, availability, and enhanced catalyst system activity. Exemplary chromium(III) compounds include, but are not limited to, chromium carboxylates, chromium naphthenates, chromium halides, chromium pyrrolides, and/or chromium dionates. Specific exemplary chromium(III) compounds include, but are not limited to, chromium(III) 2,2,6,6,-tetramethylheptanedionate [Cr(TMHD)$_3$], chromium(III) 2-ethylhexanoate [Cr(EH)$_3$, also referred to as chromium(III) tris(2-ethylhexanoate),] chromium(III) naphthenate [Cr(NP)$_3$], chromium(III) chloride, chromic bromide, chromic fluoride, chromium(III) acetylacetonate, chromium(III) acetate, chromium(III) butyrate, chromium (III) neopentanoate, chromium(III) laurate, chromium(III) stearate, chromium(III) pyrrolides and/or chromium(III) oxalate.

Specific exemplary chromium(II) compounds include, but are not limited to, chromous bromide, chromous fluoride, chromous chloride, chromium(II) bis(2-ethylhexanoate), chromium(II) acetate, chromium(II) butyrate, chromium(II) neopentanoate, chromium(II) laurate, chromium(II) stearate, chromium(II) oxalate and/or chromium(II) pyrrolides.

The pyrrole-containing compound can be any pyrrole-containing compound, or pyrrolide, that will react with a chromium source to form a chromium pyrrolide complex. As used in this disclosure, the term "pyrrole-containing compound" refers to hydrogen pyrrolide, i.e., pyrrole ($C_4H_5N$), derivatives of hydrogen pyrrolide, substituted pyrrolides, as well as metal pyrrolide complexes. A "pyrrolide" is defined as a compound comprising a 5-membered, nitrogen-containing heterocycle, such as for example, pyrrole, derivatives of pyrrole, and mixtures thereof. Broadly, the pyrrole-containing compound can be pyrrole and/or any heteroleptic or homoleptic metal complex or salt, containing a pyrrolide radical, or ligand. The pyrrole-containing compound can be either affirmatively added to the reaction, or generated in-situ.

Generally, the pyrrole-containing compound will have from about 4 to about 20 carbon atoms per molecule. Exemplary pyrrolides are selected from the group consisting of hydrogen pyrrolide (pyrrole), lithium pyrrolide, sodium pyrrolide, potassium pyrrolide, cesium pyrrolide, and/or the salts of substituted pyrrolides, because of high reactivity and activity with the other reactants. Examples of substituted pyrrolides include, but are not limited to, pyrrole-2-carboxylic acid, 2-acetylpyrrole, pyrrole-2-carboxyaldehyde, tetrahydroindole, 2,5-dimethylpyrrole, 2,4-dimethyl-3-ethylpyrrole, 3-acetyl-2,4-dimethylpyrrole, ethyl-2,4-dimethyl-5-(ethoxycarbonyl)-3-pyrrole-proprionate, ethyl-3,5-dimethyl-2-pyrrolecarboxylate, and mixtures thereof. When the pyrrole-containing compound contains chromium, the resultant chromium compound can be called a chromium pyrrolide.

The most preferred pyrrole-containing compounds used in a trimerization catalyst system are selected from the group consisting of hydrogen pyrrolide, i.e., pyrrole ($C_4H_5N$), 2,5-dimethylpyrrole and/or chromium pyrrolides because of enhanced trimerization activity. Optionally, for ease of use, a chromium pyrrolide can provide both the chromium source and the pyrrole-containing compound. As used in this disclosure, when a chromium pyrrolide is used to form a catalyst system, a chromium pyrrolide is considered to provide both the chromium source and the pyrrole-containing compound. While all pyrrole-containing compounds can produce catalyst systems with high activity and productivity, use of pyrrole and/or 2,5-dimethylpyrrole can produce a catalyst system with enhanced activity and selectivity to a desired product(s).

The metal alkyl can be any heteroleptic or homoleptic metal alkyl compound. One or more metal alkyls can be used. The alkyl ligand(s) on the metal can be aliphatic and/or aromatic. Preferably, the alkyl ligand(s) are any saturated or unsaturated aliphatic radical. The metal alkyl can have any number of carbon atoms. However, due to commercial availability and ease of use, the metal alkyl will usually comprise less than about 70 carbon atoms per metal alkyl molecule and preferably less than about 20 carbon atoms per molecule. Exemplary metal alkyls include, but are not limited to, alkylaluminum compounds, alkylboron compounds, alkyl magnesium compounds, alkyl zinc compounds and/or alkyl lithium compounds. Exemplary metal alkyls include, but are not limited to, n-butyl lithium, s-butyllithium, t-butyllithium, diethylmagnesium, diethylzinc, triethylaluminum, trimethylaluminum, triisobutylalumium, and mixtures thereof.

Preferably, the metal alkyl is selected from the group consisting of non-hydrolyzed, i.e., not pre-contacted with water, alkylaluminum compounds, derivatives of alkylaluminum compounds, halogenated alkylaluminum compounds, and mixtures thereof for improved product selectivity, as well as improved catalyst system reactivity, activity, and/or productivity. The use of hydrolyzed metal alkyls can result in decreased olefin, i.e., liquids, production and increased polymer, i.e., solids, production.

Most preferably, the metal alkyl is a non-hydrolyzed alkylaluminum compound, expressed by the general formulae $AlR_3$, $AlR_2X$, $AlRX_2$, $AlR_2OR$, $AlRXOR$, and/or $Al_2R_3X_3$, wherein R is an alkyl group and X is a halogen atom. Exemplary compounds include, but are not limited to, triethylaluminum, tripropylaluminum, tributylaluminum, diethylaluminum chloride, diethylaluminum bromide, diethylaluminum ethoxide, diethylaluminum phenoxide, ethylaluminum dichloride, ethylaluminum sesquichloride, and mixtures thereof for best catalyst system activity and product selectivity. The most preferred alkylaluminum compound is triethylaluminum, for best results in catalyst system activity and product selectivity.

Usually, contacting and/or reacting of the chromium source, pyrrole-containing compound and a metal alkyl is done in an unsaturated hydrocarbon and can be done in any manner known in the art. For example, a pyrrole-containing compound can be contacted with a chromium source and then with a metal alkyl. Optionally, a pyrrole-containing compound can be contacted with a metal alkyl and then with a chromium source. Numerous other contacting procedures can be used, such as for example, contacting all catalyst system components in the trimerization reactor.

The unsaturated hydrocarbon can be any aromatic or aliphatic hydrocarbon, in a gas, liquid or solid state. Preferably, to effect thorough contacting of the chromium source, pyrrole-containing compound, and metal alkyl, the unsaturated hydrocarbon will be in a liquid state. The unsaturated hydrocarbon can have any number of carbon atoms per molecule. Usually, the unsaturated hydrocarbon will comprise less than about 70 carbon atoms per molecule, and preferably, less than about 20 carbon atoms per molecule, due to commercial availability and ease of use. Exemplary unsaturated, aliphatic hydrocarbon compounds include, but are not limited to, ethylene, 1-hexene, 1,3-butadiene, and mixtures thereof. The most preferred unsaturated aliphatic hydrocarbon compound is 1-hexene, because of elimination of catalyst system preparation steps and 1-hexene can be a reaction product. Exemplary unsaturated aromatic hydrocarbons include, but are not limited to, toluene, benzene, xylene, ethylbenzene, mesitylene, hexamethylbenzene, and mixtures thereof. Unsaturated, aromatic hydrocarbons are preferred in order to improve catalyst system stability, as well as produce a highly active and selective catalyst system. The most preferred unsaturated aromatic hydrocarbon is selected from the group consisting of toluene and ethylbenzene, with ethylbenzene most preferred for best catalyst system activity and product selectivity, as well as ease of use.

Optionally, and preferably, a halide source is also present in the catalyst system composition. The presence of a halide source in the catalyst system composition can increase catalyst system activity and productivity, as well as increase product selectivity. Exemplary halides include, but are not limited to fluoride, chloride, bromide, and/or iodide. Due to ease of use and availability, chloride is the preferred halide. Based on improved activity, productivity, and/or selectivity, bromide is the most preferred halide.

The halide source can be any compound containing a halogen. Exemplary compounds include, but are not limited to, compounds with a general formula of $R_mX_n$, wherein R can be any organic and/or inorganic radical, X can be a halide, selected from the group consisting of fluoride, chloride, bromide, and/or iodide, and m+n can be any number greater than 0. If R is an organic radical, preferably R has from about 1 to about 70 carbon atoms per radical and, most preferably from 1 to 20 carbon atoms per radical, for best compatibility and catalyst system activity. If R is an inorganic radical, preferably R is selected from the group consisting of aluminum, silicon, germanium, hydrogen, boron, lithium, tin, gallium, indium, lead, and mixtures thereof. Specific exemplary compounds include, but are not limited to, methylene chloride, chloroform, benzylchloride, silicon tetrachloride, tin(II) chloride, tin(IV) chloride, germanium tetrachloride, boron trichloride, aluminum tribromide, aluminum trichloride, 1,4-di-bromobutane, and/or 1-bromobutane. Most preferably, the halide source is selected from the group consisting of tin (IV) halides, germanium halides, and mixtures thereof.

Furthermore, the chromium source, the metal alkyl and/or unsaturated hydrocarbon can contain and provide a halide to the reaction mixture. Preferably, if a halide is present, the halide source is an alkylaluminum halide and is used in conjunction with alkylaluminum compounds due to ease of use and compatibility, as well as improved catalyst system activity and product selectivity. Exemplary alkylaluminum halides include, but are not limited to, diisobutylaluminum chloride, diethylaluminum chloride, ethylaluminum sesquichloride, ethylaluminum dichloride, diethylaluminum bromide, diethylaluminum iodide, and mixtures thereof.

It should be recognized, however, that the reaction mixture comprising a chromium source, pyrrole-containing compound, metal alkyl, unsaturated hydrocarbon and optionally a halide can contain additional components which do not adversely affect and can enhance the resultant catalyst system.

Reactants

Trimerization, as used in this disclosure, is defined as the combination of any two, three, or more olefins, wherein the number of olefin, i.e., carbon-carbon double bonds is reduced by two. Reactants applicable for use in the trimerization process of this invention are olefinic compounds which can a) self-react, i.e., trimerize, to give useful products such as, for example, the self reaction of ethylene can give 1-hexene and the self-reaction of 1,3-butadiene can give 1,5-cyclooctadiene; and/or b) olefinic compounds which can react with other olefinic compounds, i.e., co-trimerize, to give useful products such as, for example, co-trimerization of ethylene plus hexene can give 1-decene and/or 1-tetradecene, co-trimerization of ethylene and 1-butene can give 1-octene, co-trimerization of 1-decene and ethylene can give 1-tetradecene and/or 1-docosene. For example, the number of olein bonds in the combination of three ethylene units is reduced by two, to one olefin bond, in 1-hexene. In another example, the number of olefin bonds in the combination of two 1,3-butadiene units, is reduced by two, to two olefin bonds in 1,5-cyclooctadiene. As used herein, the term "timerization" is intended to include dimerization of diolefins, as well as "co-trimerization", both as defined above.

Suitable trimerizable olefin compounds are those compounds having from about 2 to about 30 carbon atoms per molecule and having at least one olefinic double bond. Exemplary mono-1-olefin compounds include, but are not limited to acyclic cyclic olefins such as, for example, ethylene, propylene, 1-butene, 2-butene isobutylene, 1-pentene, 2-pentene, 1-hexene, 2-hexene, 3-hexene, 1-heptene, 2-heptene, 3-heptene, the four normal octenes, the four normal nonenes, and mixtures of any two or more thereof. Exemplary diolefin compounds include, but are not limited to, 1,3-butadiene, 1,4-pentadiene, and 1,5-hexadiene. If branched and/or cyclic olefins are used as reactants, while not wishing to be bound by theory, it is believed that steric hindrance could hinder the trimerization process. Therefore, the branch and/or cyclic portion(s) of the olefin preferably should be distant from the carbon-carbon double bond.

Catalyst systems produced in accordance with this invention preferably are employed as trimerization catalyst systems.

Products

The olefinic products of this invention have established utility in a wide variety of applications, such as, for example, as monomers for use in the preparation of homopolymers, copolymers, and/or terpolymers. The olefinic products of this invention can have from about 6 to about 100 carbon atoms per molecule. As discussed previously, trimerization of ethylene can yield hexenes, preferably 1-hexene. Trimerization of ethylene and 1-hexene can produce decenes, preferably 1-decene. Trimerization of 1,3-butadiene can produce 1,5-cyclooctadiene.

Drawings

A further understanding of some of the aspects of this invention can be found by referring to the attached schematic flow diagrams, in combination with the following descriptions. Various additional pumps, valves, heaters, coolers and other conventional equipment necessary for the practice of this invention will be familiar to one skilled in the art. Said additional equipment has been omitted from the drawings for the sake of clarity. The descriptions of the drawings provide one method for operating the process. However, it is understood that while these drawings are general representations of the process, minor changes can be made in adapting the drawings to the various conditions within the scope of the invention. It is also understood that numerical references in the drawings are consistent throughout the drawings. For example, inlet line 1, an olefin and optionally hydrogen inlet line, is an olefin and optionally hydrogen inlet line in all drawings.

As used in this disclosure, "olefin feed" refers to compounds more fully defined in the "Reactant" portion of this disclosure, such as, for example, ethylene, propylene, and/or 1-hexene. "Solvent" refers to a diluent or medium in which the trimerization process occurs; however, by no means is the solvent necessarily an inert material; it is possible that the solvent can contribute to a trimerization reaction process. Exemplary solvents include, but are not limited to, cyclohexane, methylcyclohexane, isobutane, 1-hexene, and mixtures of two or more thereof. "Reactor effluent" refers to all components that can be present in and can be removed from a trimerization reactor, including, but not limited to, unreacted olefin, catalyst system, trimerization product(s) and/or reaction co-product(s), also referred to as reaction by-product(s). "Catalyst kill" refers to those compounds which can deactivate, either partially or completely, catalyst system used in the trimerization process. "Heavies" refers to reaction co-product(s) which have a higher molecular weight than olefin reactants and/or the desired trimerization reaction product(s), and include higher olefinic products, such as, for example decenes and tetradecenes, as well as polymeric products.

Referring to FIG. 1, olefin feed, and optionally hydrogen, is fed through inlet line 1 into trimerization reactor 4. Inlet line 2 introduces catalyst system and optionally, solvent into trimerization reactor 4. Inlet line 3, an optional embodiment of the invention, can supply olefin feed from a second source, such as, for example an ethylene effluent, or discharge, stream from a polyethylene polymerization production facility. Trimerization reactor effluent comprising trimerized product(s), reaction co-product(s), unreacted olefin, catalyst system, and other reactor components is removed via effluent line 6. Catalyst system deactivation, i.e., "kill", components, if desired are fed via inlet line 5 into effluent line 6. It should be noted that lines 1, 2, 3, and 6 can be located anywhere on trimerization reactor 4. However, the location of lines 1, 2, and 3 must allow olefin feed stream to thoroughly contact catalyst system from line 2 in trimerization reactor 4. Filter 7 is an optional embodiment of the invention which can remove particulates, such as, for example, catalyst fines and undesirable polymeric products, from effluent line 6. For example, if the reactor effluent stream in effluent line 6 is maintained at a higher temperature, fewer particulates, such as, for example particulates resulting from undesirable polymer product(s), can form and filter 7 may not be necessary. While not wishing to be bound by theory, it is believed that higher reactor and line temperatures can inhibit solidification of undesirable polymer particles, i.e., higher temperatures can keep undesirable polymer particles from precipitating. However, if the reactor effluent stream in effluent line 6 is allowed to cool and particulates can form, filter 7 can be used. Line 8 can be either filter 7 effluent or a continuation of effluent line 6 and line 8 comprises little or no particulates. Inlet line 9 is a further optional embodiment of the invention and can include a stream of heavies to be separated, such as, for example a discharge effluent stream from a polyethylene production plant. Separator 10 separates catalyst system and other heavies from lighter olefins. Effluent line 12 is an effluent stream comprising catalyst system and other heavy olefins from separator 10. Effluent line 11 also is an effluent stream from separator 10 and can be used to recover light olefins, including trimerized products. Separator 13 can be used to separate trimerized products from olefin reactants via effluent line 14 and solvent via effluent line 15. Separator 16 can be used to separate desired trimerization product(s) via effluent line 17 from trimerization reaction solvent via effluent line 18. Separator 19 can be used to separate trimerization reaction solvent via effluent line 20 for reuse or recycle from other components which can be removed via effluent line 21.

Figure 2:
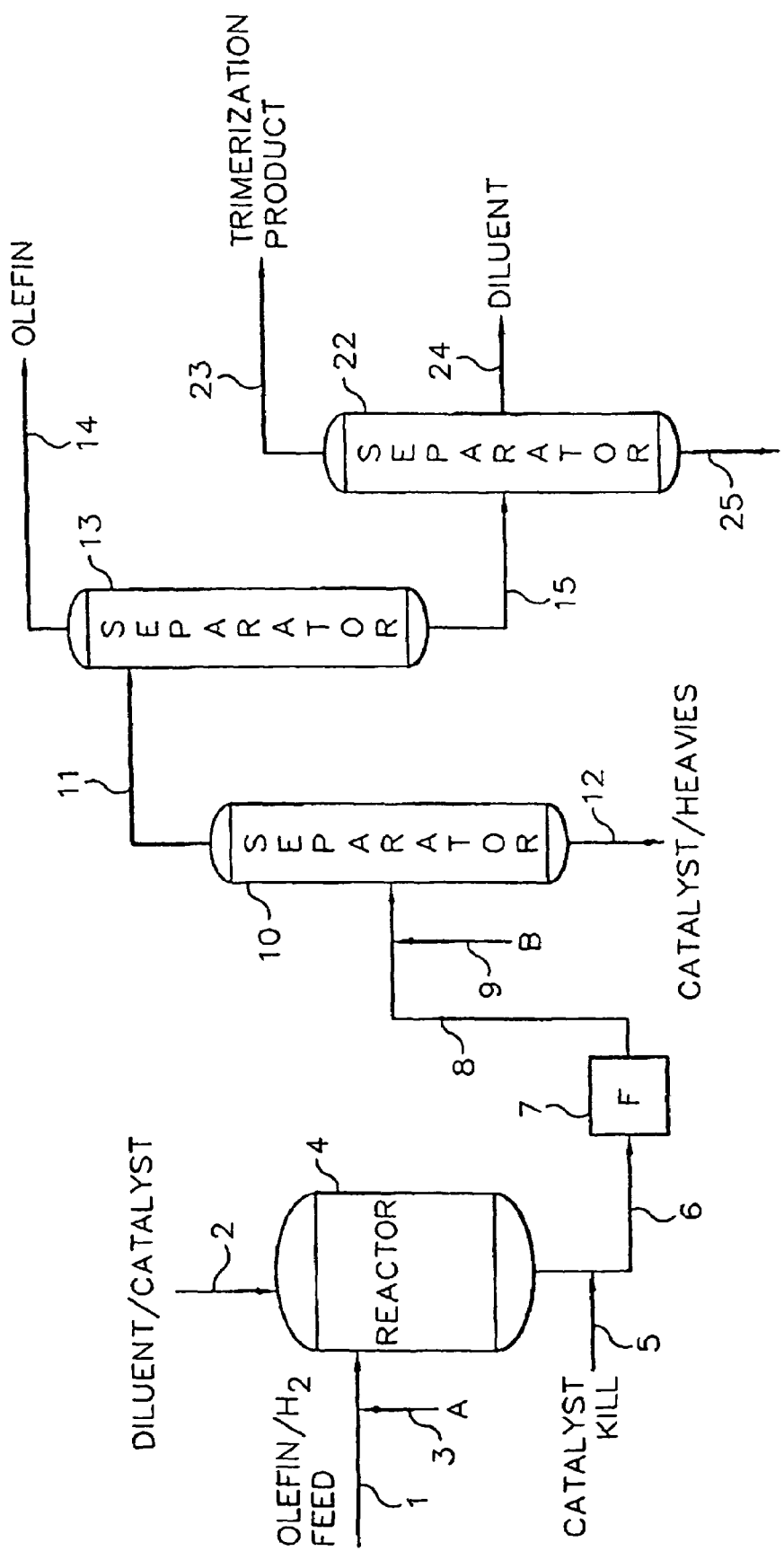
FIG. 2 is a schematic representation of another embodiment of an olefin trimerization process using one separator after olefin removal.

Referring now to FIG. 2, another embodiment of the invention, wherein like numbers represent like components, separator 22 and lines 23, 24, and 25 are added. Separator 22 can be used to separate trimerization product(s) via effluent line 23 from trimerization reaction solvent via effluent line 24 and any other remaining reaction components via effluent line 25.

Figure 3:
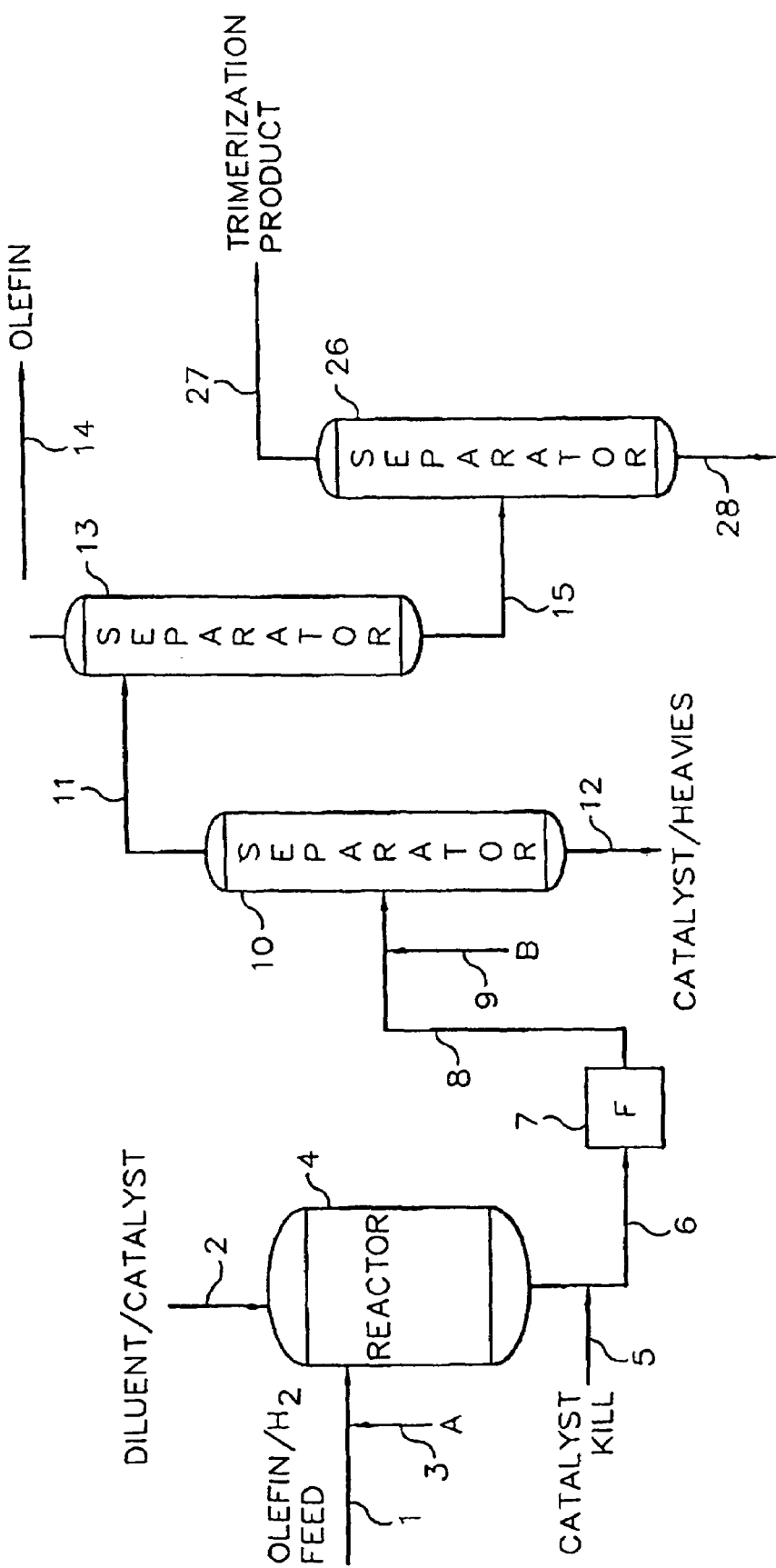
FIG. 3 is a schematic representation of a further embodiment of an olefin trimerization process using a solventless trimerization reaction system.

Referring now to FIG. 3, another embodiment of the invention, wherein like numbers represent like components and wherein a solvent is not used during the trimerization process. Therefore, separator 26 is used to separate trimerization product(s) via effluent line 27 from all other remaining components removed via effluent line 28.

Figure 4:
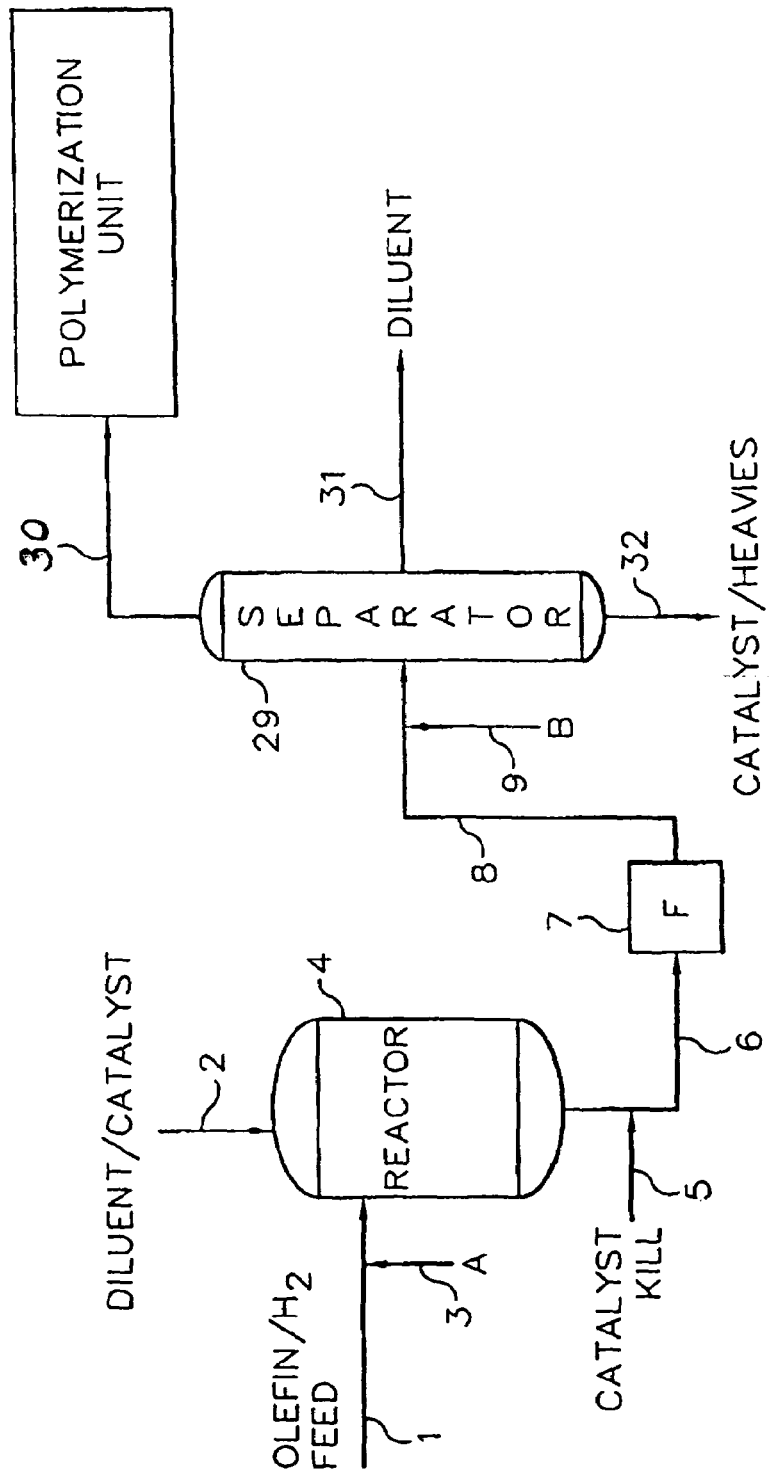
FIG. 4 is a schematic representation of yet a further embodiment of an olefin trimerization process wherein reactant and trimerized product(s) are sent directly to an olefin polymerization unit.

Referring now to FIG. 4, another embodiment of the invention wherein like numbers represent like components, separator 29 is used to separate olefin feed and trimerization product(s) via effluent line 30. If desired, olefin feed and trimerization product(s) can be fed directly to an olefin polymerization unit where an olefin feed and trimerized product(s) are polymerized to form a copolymer, such as, or example an ethylene hexene copolymer. Solvent, if present in trimerization reactor 4, can be removed from separator 29 via effluent line 31. Effluent line 32 removes excess and/or deactivated catalyst system and other heavies which can be produced during the trimerization reaction.

Referring to FIG. 5, again like numbers represent like system components, separator 33 is used to recover any unreacted olefin feed via effluent line 34. Effluent line 35 carries all non-recovered olefin products to separator 37. Inlet line 36 is similar to inlet line 9 in previous drawings wherein a stream of heavies from another location, such as, for example a polyethylene plant, is added for separation. Separator 37 can be used to separate trimerization product(s) via effluent line 38, solvent via effluent line 39, and catalyst and other products via effluent line 40.

Figure 6:
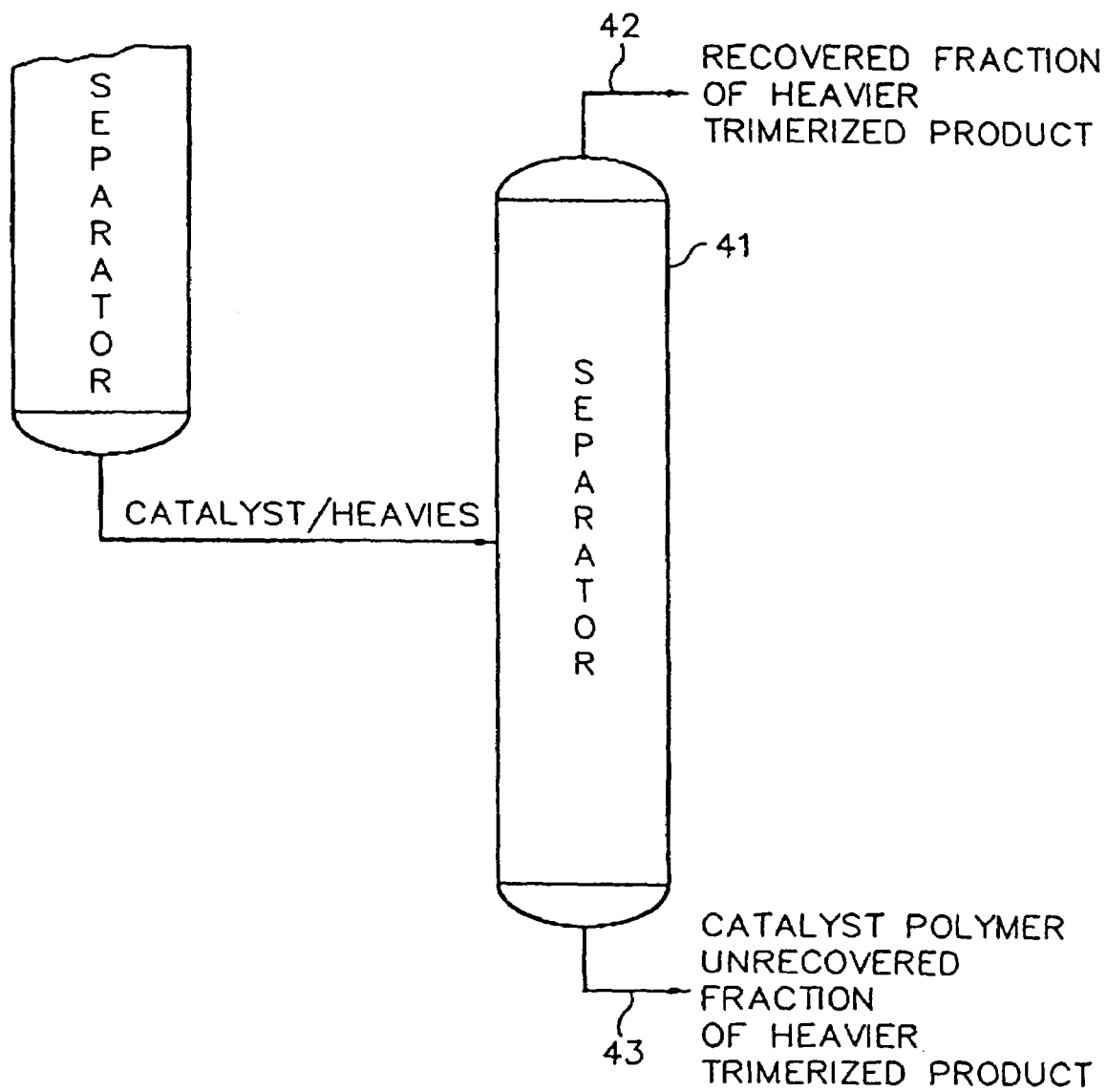
FIG. 6 is a schematic representation of yet another embodiment of an olefin trimerization process wherein catalyst system and reactor heavies stream(s) can undergo further product separation. While these drawings describe embodiments of the invention for the purpose of illustration, the invention is not to be construed as limited by the drawings but the drawings are intended to cover all changes and modifications within the spirit and scope thereof.

Referring now to FIG. 6, another embodiment of the invention, wherein like numbers represent like components and wherein a catalyst system and heavies effluent line can be fed to separator 41 to separate trimerization reaction by-products, such as decenes via effluent line 42 from other reactor effluent components via effluent line 43, such as, for example catalyst system, polymer particulates, other higher olefinic by-products, including some decenes. It should be noted that some of the decenes must be kept in effluent line 43 in order to maintain flowability of catalyst system effluent and/or discharge products and possible polymer particulates, if not removed previously in filter 7. Decenes removed via effluent line 42 can be recovered or routed for additional use, such as hydrogenation to commercially useful products such as Soltrol® 100.

Figure 5:
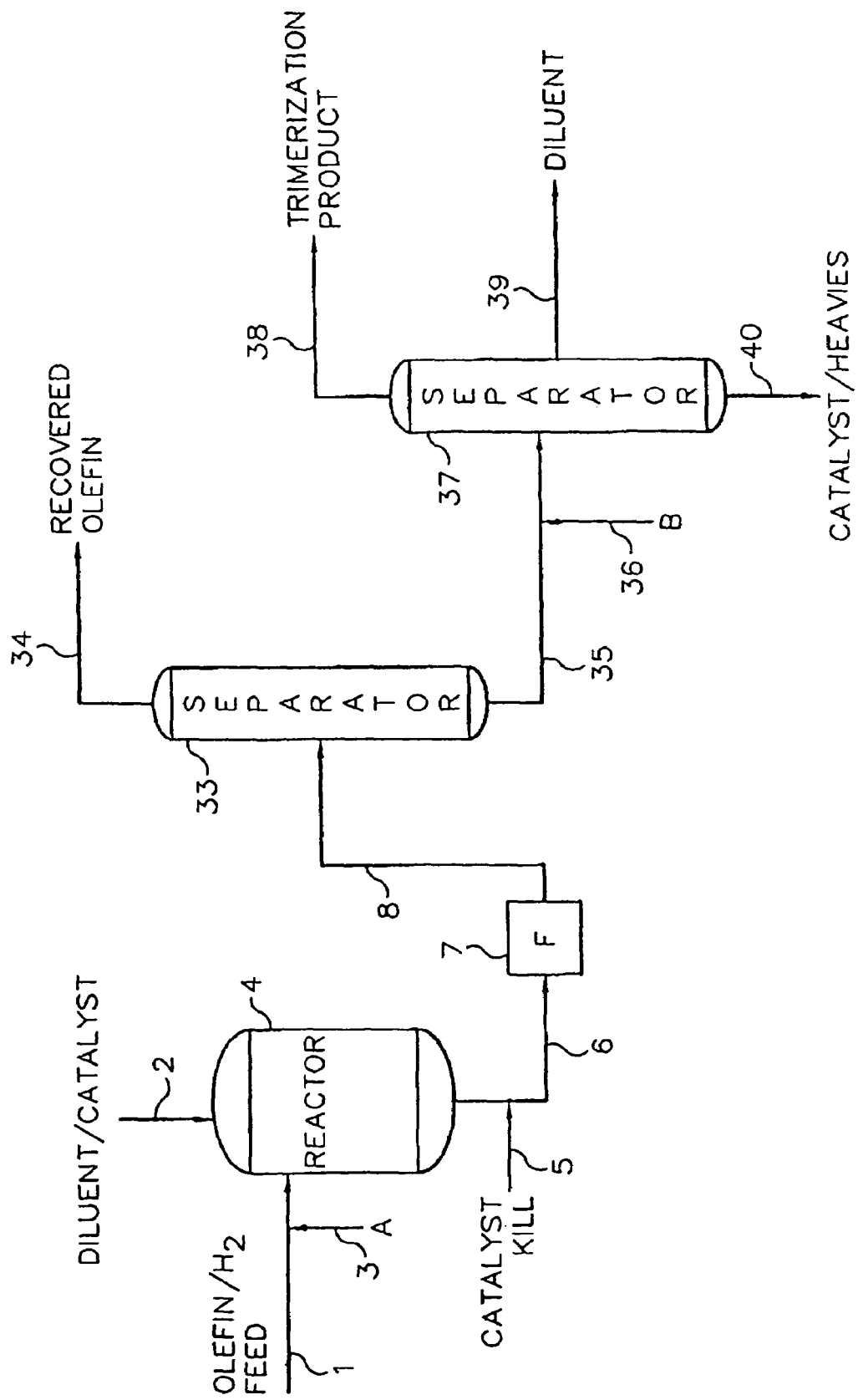
FIG. 5 is a schematic representation of still another embodiment of an olefin trimerization process wherein catalyst system and reactor heavies are removed after a separation sequence; other embodiments, such as, for example, include use of two columns to separate trimerized product(s), as in FIG. 1, or a solventless system, as in FIG. 3, can be employed as variations.

Note that the invention is not limited only to the embodiments specifically shown in the figures. For example FIG. 5 shows one separator 37 after an olefin removal separator 33. Other variants, such as using two separator columns to separate trimerized product(s) and solvent, such as in FIG. 1 with separator 16 and separator 19, can be used or solvent removal may not be necessary, as shown in FIG. 3 with separator 26.

Reaction Conditions

Reaction products, i.e., olefin trimers as disclosed in this specification, can be prepared with the disclosed catalyst systems by solution reaction, slurry reaction, and/or gas phase reaction techniques using conventional equipment and contacting processes. Contacting of the olefin feed with a catalyst system can be effected by any manner known in the art. One convenient method is to suspend the catalyst system in a solvent, i.e., diluent or medium, and to agitate the mixture to maintain a uniform catalyst system concentration throughout the reaction mixture and/or maintain the catalyst system in solution throughout the trimerization process. Other known contacting methods can also be employed.

A trimerization process can be carried out in an inert solvent, such as a paraffin, cycloparaffin, or aromatic hydrocarbon. Exemplary reactor diluents include, but are not limited to, isobutane, cyclohexane and methylcyclohexane. Isobutane can be used to improve process compatibility with other known olefin production processes. However, a homogenous trimerization catalyst system can be more soluble in cyclohexane. Therefore, a preferred solvent for a homogeneous catalyzed trimerization process is cyclohexane.

Alternatively, a "solventless" reaction system can be used. In a solventless system, reaction product can be the reactor "solvent" or diluent. For example, if ethylene is trimerized to 1-hexene, 1-hexene can be used in the reactor as a solvent, or diluent. A solventless reaction system is preferred in that fewer separation steps can be used following completion of the trimerization reaction.

Reaction temperatures and pressures can be any temperature and pressure which can trimerize the olefin reactants. When the reactant is predominately ethylene, a temperature in the range of about 0° to about 300° C. (about 32° to about 575° F.) generally can be used. Preferably, when the reactant is predominately ethylene, a temperature in the range of about 60° to about 275° C. (about 140° to about 530° F.) is employed. Most preferably, reactor temperature is within a range of 110° to 125° C. (235° to 255° F.). Reactor temperatures that are too low can cause polymeric products to precipitate out of the process can decrease product selectivity by increasing the production of polymeric products. Reactor temperatures that are too high can decrease catalyst system activity, negatively affect reaction selectivity and can cause decomposition of the catalyst system and reaction products. However, reactor temperature range s can vary if other solvents are used in the trimerization process.

Generally, reaction pressures are within a range of about atmospheric to about 2500 psig. Selection of reaction pressure depends on the solvent, or diluent, used in the reactor. Preferably, when using a diluent other than 1-hexene, reaction pressures within a range of about atmospheric to about 1500 psig and most preferably, within a range of 600 to 1000 psig are employed. Preferably, when using 1-hexene as the diluent, reaction pressures within a range of about atmospheric to about 2000 psig and most preferably, within a range of 1100 to 1600 psig are employed. Too low of a reaction pressure can result in low catalyst system activity.

Optionally, hydrogen can be added to the reactor to enhance product selectivity, i.e., reduce formation of polymeric products.

A further understanding of the present invention and its advantages also will be provided by reference to the following examples.

EXAMPLES

Example 1

This example shows different methods of preparing trimerization catalyst systems and the trimerization results. Runs 101–106 demonstrate catalyst system preparation outside of the trimerization reactor and feeding catalyst system into the trimerization reactor. Runs 107–109 demonstrate a catalyst system preparation method inside the trimerization reactor. Runs 110–112 demonstrate another catalyst system preparation method inside the trimerization reactor. All catalyst system preparation was carried out under an inert atmosphere (nitrogen or helium) using standard Schlenk techniques, if applicable. All solvents, or diluents, were dried over mole sieves/alumina and purged with nitrogen before use. The components used to prepare the catalyst systems and the molar ratios of chromium to other catalyst system components are listed in Table 1.

Catalyst systems used in Runs 101–106 were prepared by dissolving chromium tris(2-ethylhexanoate) [$Cr(EH)_3$] in toluene or ethylbenzene (40 ml/g $Cr(EH)_3$). In a separate container, triethylaluminum (TEA) and a chloride source were mixed together. 2,5-Dimethylpyrrole (DMP) was added to either the $Cr(EH)_3$ solution or the aluminum alkyl-chloride source. The chromium mixture, either with or without DMP, depending on the preparation method selected above, was added to the aluminum mixture and the resulting brown-yellow solution was stirred for a time within a range of 10 minutes to one (1) hour. The resulting solution then was filtered through a celite frit and was diluted to the desired concentration.

Catalyst systems used in Runs 107–109 were prepared by dissolving $Cr(EH)_3$ in cyclohexane and diluting to the desired concentration with additional cyclohexane. This solution was charged to a catalyst feed tank to the reactor. TEA and chloride sources were mixed together in 200 ml of cyclohexane. DMP was added to the aluminum alkyl/chloride source and allowed to react for 5 minutes. This solution, along with the solvent for that particular run, was charged to a solvent feed tank to the reactor. Thus, the aluminum alkyl/chloride source/DMP mixture was fed to the reactor in the same stream as the reactor solvent, but separately from the chromium source.

Catalyst systems used in Runs 110–112 were prepared by dissolving $Cr(EH)_3$ in cyclohexane and diluting to the desired concentration with additional cyclohexane. This solution was charged to a catalyst feed tank to the reactor. TEA and chloride sources were mixed together in 100 ml of cyclohexane. DMP was added to the aluminum alkyl/chloride source and allowed to react for 5 minutes. The resulting aluminum alkyl/chloride source/DMP solution was diluted to the desired concentration with additional cyclohexane and then charged an aluminum feed tank to the reactor. Thus, the aluminum alkyl/chloride source/DMP mixture was fed to the reactor in a separate stream from either the reactor solvent or the chromium source.

All trimerization reactions disclosed in Runs 101–112 can be considered continuous feed reactions, i.e., not batch reactions. The feed rates and temperatures of all Runs are given in Table 2. Reactor volume in Runs 101, 105 and 110–112 was 0.264 gallons; reactor volume in all other Runs was one (1) gallon. Reactor pressure in Run 102 was 1465 psia; reactor pressure in all other Runs was 800 psia. The temperature and pressure of the reactor were continuously controlled at the desired values. Reactor temperature was controlled by an internal coiled pipe. Each Run sequence was started by turning on a solvent pump to fill the autoclave reactor and heating the reactor to the desired temperature. The reactor was purged with the solvent shown in Table 2 for 30 minutes. Additional process conditions are given in Table 1.

In Runs 101–107, catalyst system was fed to the reactor at double the desired rate for 30 minutes prior to the introduction of ethylene and then reduced to the desired feed rate. In Runs 101 and 103–106, solvent feed continued during catalyst system feed and ethylene/hydrogen mixture feed. In Run 102, 1-hexene was fed with catalyst system until the addition of the ethylene/hydrogen mixture; 1-hexene feed was stopped when the ethylene/hydrogen mixture feed began.

In Runs 107–109, two different reactor inlets simultaneously fed a) a catalyst system portion comprising a Cr(EH)$_3$ solution and b) solvent and another catalyst system portion comprising an aluminum alkyl/chloride source/DMP solution.

In Runs 110–112, three different reactor inlets simultaneously fed a) a catalyst system portion comprising a Cr(EH)$_3$ solution, b) another catalyst system portion comprising an aluminum alkyl/chloride source/DMP solution, and c) solvent.

Upon exit from the reactor, the catalyst/product solution stream was deactivated with an alcohol, cooled and filtered in a pressure vessel through a steel sponge filter material to remove polymeric solids. The product stream was taken to a product storage tank.

Each reaction was monitored for 6 hours. On-line samples were collected once every hour and analyzed by gas chromatography to determine reactor effluent composition. Product analyses are given in Table 2.

Example 2

These examples demonstrate the process of trimerizing ethylene to make 1-hexene and the separation steps necessary to produce the desired product purity.

Greater than 98.5% purity 1-hexene was produced in Runs 201–203 in the following manner. Ethylene and catalyst system were fed to a reactor in the presence of a diluent/solvent. The reactor effluent was stripped of ethylene in column 1. Subsequently, 1-hexene product was removed from the diluent/solvent, spent catalyst, and other heavier co-products in column 2. Finally, spent catalyst and other heavies were removed from the diluent/solvent in column 3. The diluent/solvent then was returned to the reactor.

The reactor was liquid full and had a volume of 10 gallons. Columns 1, 2, and 3 were packed towers. The diluent/solvent was methylcyclohexane. The reactor pressure used was 800 psig (5516 Kpa).

TABLE 1

Catalyst Components and Process Conditions

| Run | Moles/mole Cr DMP | TEA | Chloride | Chloride Source | Solvent | Reactor Temp, °C. | Catalyst Concent. MgCr/ml | Catalyst Feed Rate, ml/hr | Al Feed Rate, ml/hr | C$_2$ = Feed Rate, g/hr | Solvent Feed Rate, gallons/hr | H$_2$ Feed Rate, l/hr |
|---|---|---|---|---|---|---|---|---|---|---|---|---|
| 101 | 3.0 | 11.0 | 8.0 | DEAC | Isobutane | 100 | 0.35 | 45 | — | 275 | 0.60 | 4.40 |
| 102 | 1.8 | 9.0 | 2.5 | EADC | 1-Hexene | 115 | 0.50 | 30 | — | 1570 | 0.00 | 15.7 |
| 103 | 1.8 | 6.5 | 5.0 | DEAC | Cyclohexane | 115 | 0.80 | 30 | — | 1430 | 1.20 | 5.20 |
| 104 | 3.0 | 11.0 | 8.0 | DEAC | Cyclohexane | 115 | 0.17 | 30 | — | 1450 | 1.35 | 4.10 |
| 105 | 3.0 | 11.0 | 8.0 | DEAC | n-Heptane | 120 | 0.25 | 30 | — | 560 | 0.50 | 3.10 |
| 106 | 3.0 | 11.0 | 8.0 | DEAC | Methyl-cyclohexane In-situ —Al in solvent | 128 | 1.01 | 45 | — | 1640 | 1.35 | 8.20 |
| 107 | 3.0 | 11.0 | 8.0 | DEAC | Cyclohexane | 115 | 0.33 | 30 | — | 1430 | 1.20 | 5.20 |
| 108 | 3.0 | 19.0 | 1.3 | C2C16 | Cyclohexane | 115 | 0.33 | 30 | — | 1430 | 1.20 | 5.20 |
| 109 | 16.0 | 50.0 | 63.0 | DEAC | Cyclohexane In-situ —Al in Tank | 115 | 0.04 | 30 | — | 1430 | 1.20 | 5.20 |
| 110 | 3.0 | 11.0 | 8.0 | DEAC | Cyclohexane | 120 | .29 | 25 | 25 | 550 | 0.40 | 3.10 |
| 111 | 3.0 | 11.0 | 8.0 | DEAC | Cyclohexane | 120 | .29 | 25 | 25 | 550 | 0.40 | 3.10 |
| 112 | 3.0 | 11.0 | 8.0 | DEAC | Cyclohexane | 120 | .29 | 25 | 25 | 550 | 0.40 | 3.10 |

TABLE 2

Product Analysis (weight percents)

| Run | % Butenes | % 1-Hexene | % Internal Hexenes | Hexene Purity, % | % Octenes | % Decenes | % Ethylene Conversion | Polymer Produced, g | Productivity, g olefin/g Cr-hr | Productivity, g olefin/g Metals - hr |
|---|---|---|---|---|---|---|---|---|---|---|
| 101 | <0.1 | 93.7 | 1.4 | 98.6 | 0.3 | 4.6 | 42.3 | 0.4 | 7000 | 640 |
| 102 | 0.4 | 88.8 | 0.8 | 99.1 | 0.5 | 8.8 | 78.1 | 2.9 | 71800 | 10300 |
| 103 | 0.1 | 84.5 | 0.7 | 99.2 | 0.2 | 13.3 | 86.6 | 2.4 | 43400 | 6220 |
| 104 | 0.1 | 94.1 | 0.4 | 99.6 | 0.3 | 5.1 | 68.0 | 1.6 | 185000 | 17000 |
| 105 | 0.1 | 91.8 | 0.8 | 99.1 | 0.3 | 6.7 | 72.0 | 0.4 | 49300 | 4540 |
| 106 | 0.3 | 85.0 | 1.5 | 98.3 | 0.4 | 11.9 | 83.2 | 1.1 | 25600 | 2350 |
| 107 | 0.1 | 92.1 | 0.4 | 99.6 | 0.3 | 6.8 | 75.9 | 2.5 | 101000 | 9300 |
| 108 | 0.2 | 79.9 | 1.5 | 98.2 | 0.4 | 16.4 | 89.9 | 1.1 | 104000 | 9550 |
| 109 | 0.1 | 96.2 | 0.6 | 99.6 | 0.3 | 3.1 | 47.2 | 1.0 | 533000 | 8940 |
| 110 | 0.2 | 91.5 | 0.6 | 99.3 | <0.1 | 7.2 | 76.5 | 0.1 | 52300 | 4810 |
| 111 | 0.2 | 93.0 | 0.6 | 99.3 | 0.1 | 5.6 | 74.9 | 0.3 | 52000 | 4790 |
| 112 | 0.2 | 92.5 | 0.7 | 99.3 | 0.2 | 6.1 | 74.6 | 0.1 | 51500 | 4740 |

Run 201

The catalyst system was prepared in the same manner as described in Example 1.

To produce 1-hexene, ethylene and methylcyclohexane were fed to the reactor at a rate of 34.9 lbs/hr and 66.7 lbs/hr average, respectively. Hydrogen was added at an average rate of 3.4 standard cubic feet per hour. Catalyst was metered into the reactor at an average rate of 256 ml/hr. The reactor temperature was 244 F. (118 C.).

At the conditions specified, 1-hexene product was removed from column 2 at an average rate of 24.9 lbs/hr. Product purity was 98.8 weight percent 1-hexene, with off hexenes being the other major components. Overall, selectivity of ethylene to 1-hexene was 85.9 weight percent.

Run 202

Catalyst system was prepared in the same manner as described in Example 2.

Ethylene and methylcyclohexane were fed to the reactor at a rate of 49.9 lbs/hr and 118.8 lbs/hr average, respectively. Hydrogen was added at an average rate of 4.1 standard cubic feet per hour. Catalyst was metered into the reactor at an average rate of 230 ml/hr. Reactor temperature was 247° F. (120° C.).

At the conditions specified, 1-hexene product was removed from column 2 at an average rate of 31.1 lbs/hr. Product purity was 99.1 weight percent 1-hexene, with off-hexenes being the other major components. Overall, selectivity of ethylene to 1-hexene was 92.1 weight percent.

Run 203

The catalyst system was prepared in the same manner as described in Example 1.

Ethylene and methylcyclohexane were fed to the reactor at a rate of 65.2 lbs/hr and 176.3 lbs/hr average, respectively. Hydrogen was added at an average rate of 6.4 standard cubic feet per hour. Catalyst was metered into the reactor at an average rate of 285 ml/hr. Reactor temperature was 264° F. (129° C.).

At the conditions specified, 1-hexene product was removed from column 2 at an average rate of 37.7 lbs/hr. Product purity was 99.3 weight percent 1-hexene, with off-hexenes being the other major components. Overall, selectivity of ethylene to 1-hexene was 94.4 weight percent.

Example 3

This example shows that coproducts of the trimerization reaction, which include decenes, can be hydrogenated and incorporated into commercially useful and available solvents, such as Soltrol® 100. Soltrol® 100 is a registered trademark of Phillips Petroleum Company and is a mix of $C_9$–$C_{11}$ isoparaffins. One embodiment of such a hydrogenation process is shown in FIG. 6.

Catalyst activation and hydrotreatment were done in a downflow 2'×¾" OD fixed-bed reactor. The reactor was charged with 15 ml of 3 mm glass beads, 20 ml of commercially available Englehard Ni5254, lot HE 38 hydrogenation catalyst, and topped with Alcoa alumina A201. Heat control was accomplished in a 3-zone tube furnace. Catalyst activation was done at 343° C. with 300 cc/min of hydrogen ($H_2$, 99.9%) for three hours prior to hydrogenation of a decene isomer fraction of the trimerization reaction co-product.

A decene isomer fraction of the trimerization reaction co-product, was hydrotreated as it was feed to the reactor by a syringe pump. Hydrogen was provided to the top of the reactor through a calibrated mass flow controller at 100 cc/min. Total pressure of 400 psig to the system was maintained at the reactor exit by a Moore regulator. Samples were periodically analyzed for bromine number and analyzed by GC and UV.

Hydrotreatment proceeded smoothly with 100% reduction of the decene to decane isomers at 1 liquid hourly spaced velocity (LHSV), 150° C., 400 psig hydrogen. However, when the LHSV was raised to 3, 150° C. and 400 psig $H_2$, total decene isomer conversion dropped to 76%. Increasing the reactor temperature to 200° C. increased conversion to 83%. Complete decene isomer conversion resulted again when the 1 LHSV, 150° C., 400 psig $H_2$ conditions were used. As is normal for hydrotreating reactions, a heat rise was noted across the reactor which was LHSV dependent. At 1 LHSV, the heat rise was 35° C.; at 3 LHSV the heat rise was 47° C. Conversion results were confirmed by GC, GC/MS and bromine number analysis. The results of these hydrogenations are listed below in Table 3.

TABLE 3

| Run | LHSV | Reactor Temp., ° C. | $H_2$ Pressure, psig | Heat Rise, ° C. | % Reduction, Decenes to Decanes |
|---|---|---|---|---|---|
| 301 | 1 | 150 | 400 | 35 | 100 |
| 302 | 3 | 150 | 400 | 47 | 76 |
| 303 | 3 | 200 | 400 | 47 | 83 |
| 304 | 1 | 150 | 400 | 35 | 100 |

A commercially available Soltrol® 100 sample, that had been hydrotreated was used to prepare blends stocks with the above hydrotreated product. Blends of $C_{10}$/Soltrol® 100 were made in 2, 10, 20, 30 and 50 volume percent concentrations to evaluate the compatibility of these two products. GC analysis, using a column that separates according to boiling points, show that the decane isomers fit into the Soltrol® 100 boiling point range. The Soltrol® 100 purity was not reduced by the addition of the hydrotreated decene product.

While this invention has been described in detail for the purpose of illustration, it is not to be construed as limited thereby but is intended to cover all changes and modifications within the spirit and scope thereof.

That which is claimed is:

1. A process for making an olefin trimerization product comprising:
   a) introducing an olefin feedstock and hydrogen into a reactor;
   b) separately introducing a catalyst system comprising a chromium source, a pyrrole-containing compound, and a metal alkyl into the reactor, thereby contacting the olefin feedstock and the catalyst system in the reactor;
   maintaining the olefin feedstock and the catalyst system under conditions to produce a reactor effluent comprising the olefin trimerization product and reactor products; and
   separating the olefin trimerization product from the reactor effluent.

2. The process according to claim 1, wherein the contacting of the olefin feedstock and the catalyst system is conducted in the presence of a diluent.

3. The process according to claim 2, wherein the diluent is selected from paraffin, cycloparaffin, an aromatic hydrocarbon, isobutane, cyclohexane, methylcyclohexane, isobutene, 1-hexene, or any combination thereof.

4. The process according to claim 2, wherein the olefin feedstock and the catalyst system are maintained at a pressure in the range of about atmospheric to about 2000 psig when the diluent comprises 1-hexene.

5. The process according to claim 2, wherein the olefin feedstock and the catalyst system are maintained at a pressure in the range of about 1100 psig to about 1600 psig when the diluent comprises 1-hexene.

6. The process according to claim 1, wherein the catalyst system is present in the reactor effluent and the process further comprises deactivating the catalyst system in the reactor effluent prior to separating the olefin trimerization product therefrom.

7. The process according to claim 1, further comprising filtering the reactor effluent prior to separating the olefin trimerization product therefrom.

8. The process according to claim 1, further comprising:
heating the reactor effluent.

9. The process according to claim 1, further comprising:
introducing heavies from a source independent of the reactor effluent into the reactor effluent; and
separating the heavies from the reactor effluent.

10. The process according to claim 1, wherein the catalyst system is present in the reactor products and the process further comprises separating the catalyst system from the reactor products.

11. The process according to claim 1, wherein the olefin feedstock comprises an olefinic compound which is self-reacting to trimerize or an olefinic compound which reacts with other olefinic compounds to form a co-trimerization product.

12. The process according to claim 1, wherein the olefin feedstock comprises one or more olefin compounds having from about 2 to about 30 carbon atoms per molecule.

13. The process according to claim 1, wherein the olefin feedstock and the catalyst system is maintained at a temperature in the range of about 0° C. to about 300° C. (about 32° F. to about 575° F.).

14. The process according to claim 1, wherein the olefin feedstock and the catalyst system are maintained at a temperature in the range of about 60° C. to about 275° C. (about 140° F. to about 530° F.).

15. The process according to claim 1, wherein the olefin feedstock and the catalyst system are maintained at a temperature in the range of about 110° C. to about 125° C. (about 235° F. to about 255° F.).

16. The process according to claim 1, wherein the olefin feedstock and the catalyst system are maintained at a pressure in the range of about atmospheric to about 2500 psig.

17. The process according to claim 1, wherein the olefin feedstock and the catalyst system are maintained at a pressure in the range of about atmospheric to about 1500 psig.

18. The process according to claim 1, wherein the olefin feedstock and the catalyst system are maintained at a pressure in the range of about 600 psig to about 1000 psig.

19. The process according to claim 1, wherein the catalyst system further comprises an inorganic oxide support.

20. The process according to claim 1, wherein the chromium source of the catalyst system comprises one or more organic or inorganic chromium compounds, wherein the chromium oxidation state is from 0 to 6.

21. The process according to claim 1, wherein the chromium source of the catalyst system comprises a compound having a general formula of $CrX_n$, wherein X is the same or different and is any organic or inorganic radical and n is an integer from 1 to 6.

22. The process according to claim 21, wherein X is an organic radical having from 1 to about 20 carbon atoms per radical.

23. The process according to claim 21, wherein X is an organic radical selected from alkyl, alkoxy, ester, ketone, amido, or any combination thereof.

24. The process according to claim 21, wherein X is an inorganic radical selected from halides, sulfates, oxides, or any combination thereof.

25. The process according to claim 1, wherein said chromium source of the catalyst system comprises a chromium(II) compound, chromium(III) compound, or a combination thereof.

26. The process according to claim 1, wherein the chromium source of the catalyst system comprises a chromium (III) compound selected from chromium carboxylates, chromium naphthenates, chromium halides, chromium pyrrolides, chromium dionates, or any combination thereof.

27. The process according to claim 1, wherein the pyrrole-containing compound of the catalyst system is reactable with the chromium source to form a chromium pyrrolide complex.

28. The process according to claim 1, wherein the pyrrole-containing compound of the catalyst system is a pyrrole, any heteroleptic or homoleptic metal complex or salt containing a pyrrolide radical or ligand, or any combination thereof.

29. The process according to claim 1, wherein the pyrrole-containing compound is hydrogen pyrrolide (pyrrole), chromium pyrrolide, lithium pyrrolide, sodium pyrrolide, potassium pyrrolide, cesium pyrrolide, salts of substituted pyrrolides, or any combination thereof.

30. The process according to claim 1, wherein the metal alkyl of the catalyst system is a heteroleptic metal alkyl compound, a homoleptic metal alkyl compound, or a combination thereof.

31. The process according to claim 1, wherein the metal alkyl of the catalyst system is alkylaluminum compounds, alkylboron compounds, alkyl magnesium compounds, alkyl zinc compounds, alkyl lithium compounds, or any combination thereof.

32. The process according to claim 1, wherein the metal alkyl of the catalyst system is a non-hydrolyzed alkylaluminum compound having a general formula of $AlR_3$, $AlR_2X$, $AlRX_2$, $AlR_2OR$, $AlRXOR$, $Al_2R_3X_3$, or any combination thereof, wherein R is an alkyl group and X is a halogen atom.

33. The process according to claim 1, wherein the chromium source, the pyrrole-containing compound, and the metal alkyl are contacted in the presence of an unsaturated hydrocarbon.

34. The process according to claim 33, wherein the unsaturated hydrocarbon is an aromatic or aliphatic hydrocarbon in the form of a gas, liquid, or solid.

35. The process according to claim 33, wherein the chromium source, the metal alkyl, the unsaturated hydrocarbon, or any combination thereof comprise a halide.

36. The process according to claim 33, wherein the unsaturated hydrocarbon is ethylene, 1-hexene, 1,3-butadiene, toluene, benzene, xylene, ethylbenzene, mesitylene, hexamethylbenzene, or any combination thereof.

37. The process according to claim 1, wherein the catalyst system further comprises a halide source.

38. The process according to claim 37, wherein the halide source has a general formula of $R_mX_n$, wherein R is an organic or inorganic radical, X is a halide radical, and m+n is a number greater than 0.

39. The process according to claim 1, wherein the chromium source, the metal alkyl, or both of the catalyst system comprise a halide.

40. In the selective conversion of olefins to olefin trimerization products a process comprising:
- a) introducing a feedstock comprising olefins and hydrogen into a reactor;
- b) separately introducing a catalyst system comprising a chromium source, a pyrrole-containing compound, and a metal alkyl into the reactor, thereby contacting the feedstock and the catalyst system in the reactor;
- c) maintaining the feedstock and catalyst system in the reactor under conditions to produce a reactor effluent comprising unreacted olefins, olefin trimerization products, catalyst, and heavies;
- d) transferring reactor effluent comprising unreacted olefins, olefin trimerization products, and heavies from the reactor to a first separator wherein catalyst and heavies are separated from the reactor effluent;
- e) removing from the first separator a first effluent stream comprising at least catalyst and heavies; and
- f) removing from the first separator a second effluent stream comprising at least unreacted olefins.

41. The process according to claim 40, wherein the reactor effluent is filtered before entering the first separator.

42. The process according to claim 40, wherein catalyst kill is introduced into the reactor effluent.

43. The process according to claim 42, wherein the reactor effluent is filtered after introduction of the catalyst kill.

44. The process according to claim 40, wherein heavies from a source independent of the reactor effluent are introduced into the reactor effluent before introduction into the first separator.

45. The process according to claim 40, wherein an effluent stream comprising olefin and trimerization product is transferred from the first separator to a second separator wherein the effluent stream is separated into a predominantly olefin effluent stream and a predominantly trimerization product effluent stream.

46. The process according to claim 45, wherein the predominantly trimerization product effluent stream is transferred from the second separator to a third separator to separate remaining heavies from the predominantly trimerization product effluent to provide a trimerization product effluent stream.

47. The process according to claim 40, further comprising:
treating the first effluent stream by recovering a portion of heavier trimerized product.

48. The process according to claim 40, wherein diluent is introduced into the reactor along with the catalyst system.

49. In the selective conversion of olefins to olefin trimerization products, a process comprising:
- a) introducing a feed stock comprising olefins and hydrogen into a reactor;
- b) separately introducing a stream comprising diluent and a catalyst system comprising a chromium source, a pyrrole-containing compound, and a metal alkyl into the reactor, thereby contacting diluent, feedstock, and catalyst system in the reactor;
- c) maintaining the feedstock and catalyst system in the reactor under conditions to produce a reactor effluent comprising diluent, unreacted olefins, olefin trimerization products, catalyst, and heavies;
- d) transferring reactor effluent comprising diluent, unreacted olefins, olefin trimerization products, and heavies from the reactor to a first separator wherein the reactor effluent is separated into 1) catalyst and heavies, 2) diluent, and 3) unreacted olefin and trimerization products;
- e) removing from the first separator a predominantly catalyst and heavies stream;
- f) removing from the first separator a predominantly diluent stream; and
- g) removing from the first separator a predominantly unreacted olefin and trimerization products stream.

* * * * *